(12) United States Patent  
Zhu et al.

(10) Patent No.: US 12,398,421 B2
(45) Date of Patent: Aug. 26, 2025

(54) NANOPORE SEQUENCING METHOD (71) Applicants: BGI SHENZHEN, Shenzhen (CN); BGI SHENZHEN CO., LTD, Shenzhen Guangdong (CN)

(72) Inventors: Guoli Zhu, Guangdong (CN); Hanjie Shen, Guangdong (CN); Jianxun Lin, Guangdong (CN); Yuan Jiang, Guangdong (CN); Tao Zeng, Guangdong (CN)

(73) Assignees: BGI SHENZHEN (CN); BGI SHENZHEN CO., LTD (CN)

( * ) Notice: Subject to any disclaimer, the term of this patent is extended or adjusted under 35 U.S.C. 154(b) by 1134 days.

(21) Appl. No.: 17/292,012

(22) PCT Filed: Dec. 7, 2018

(86) PCT No.: PCT/CN2018/119911
§ 371 (c)(1),
(2) Date: May 7, 2021

(87) PCT Pub. No.: WO2020/113581
PCT Pub. Date: Jun. 11, 2020

(65) Prior Publication Data
US 2022/0002798 A1  Jan. 6, 2022

(51) Int. Cl.
C12Q 1/68       (2018.01)
C12Q 1/6869   (2018.01)

(52) U.S. Cl.
CPC ................... C12Q 1/6869 (2013.01)

(58) Field of Classification Search
None
See application file for complete search history.

(56) References Cited

U.S. PATENT DOCUMENTS 10,246,741 B2   4/2019   Clarke et al.
11,041,194 B2   6/2021   Clarke et al.
11,136,623 B2   10/2021  Clarke et al.
(Continued)

FOREIGN PATENT DOCUMENTS

CN   101103357 A   1/2008
CN   103282518 A   9/2013
(Continued)

OTHER PUBLICATIONS

Kuhnemund et al. (Biosensors and Bioelectronics, 2015, 67: 11-17) (Year: 2015).*

(Continued)

Primary Examiner — Stephanie K Mummert
(74) Attorney, Agent, or Firm — Duane Morris LLP (57) ABSTRACT A nanopore sequencing method, including: in a nanopore sequencing device, performing rolling circle amplification by using a single-strand ring or double-strand ring of nucleic acid as a template to produce an amplified single strand; under the action of an electric field, introducing the amplified single strand into nanopores of the nanopore sequencing device, so that the amplified single strand passes through the nanopores and generates an electrical signal for each base. By determining electrical signal differences caused by different bases, a base sequence on a template nucleic acid is measured.

19 Claims, 4 Drawing Sheets

Specification includes a Sequence Listing.

(56) References Cited

U.S. PATENT DOCUMENTS

| | | |
|---|---|---|
| 2002/0197618 A1* | 12/2002 | Sampson ............ C12Q 1/6869 435/6.12 |
| 2010/0331194 A1 | 12/2010 | Turner et al. |
| 2014/0262784 A1 | 9/2014 | Clarke et al. |
| 2019/0241949 A1 | 8/2019 | Clarke et al. |
| 2019/0382834 A1 | 12/2019 | Clarke et al. |
| 2021/0087623 A1 | 3/2021 | Clarke et al. |
| 2021/0095337 A1 | 4/2021 | Clarke et al. |
| 2021/0180124 A1 | 6/2021 | Clarke et al. |

FOREIGN PATENT DOCUMENTS

| | | |
|---|---|---|
| CN | 103733063 A | 4/2014 |
| CN | 104254771 A | 12/2014 |
| CN | 104406952 A | 3/2015 |
| CN | 107002130 A | 8/2017 |
| CN | 107727705 A | 2/2018 |
| CN | 107835858 A | 3/2018 |
| WO | 2000018957 A1 | 4/2000 |
| WO | 2014066909 A1 | 5/2014 |
| WO | 12018114706 A1 | 6/2018 |

OTHER PUBLICATIONS

Hatch et al. (Genetic Analysis: Biomolecular Engineering, 1999, 15:35-40) (Year: 1999).*
Hansen et al. (J of Clin Virol, 2018, vol. 106:23-27, epub Jul. 6, 2018) (Year: 2018).*
Fuller et al. (PNAS, 2016, 113 (19):5233-5238) (Year: 2016).*
Wallace et al. (Chem Commun, 2010, 46:8195-8197) (Year: 2010).*
Chinese Patent Office, Office Action issued on Apr. 1, 2023, for corresponding Chinese Patent Application No. 201880099752.4 (English translation provided).

* cited by examiner

NANOPORE SEQUENCING METHOD

TECHNICAL FIELD

The present application relates to the technical field of sequencing, and particularly, to a nanopore sequencing method.

SEQUENCE STATEMENT

The instant application contains a Sequence Listing, which has been submitted electronically in ASCII format and is hereby incorporated by reference in its entirety. Said ASCII copy, created on Apr. 9, 2025, is named H7501-00005_ST25.txt and is 3.52 kb in size.

BACKGROUND

Due to a relatively short read length of the second-generation sequencing, it is difficult to accurately detect similar genes, SNP sites, and transcriptional isomers at present. The nanopore sequencing technology has the following characteristics: (1) single-molecule DNA sequencing, without requiring the amplification of a sequencing object, which can overcome a sequencing bias caused by gene amplification; and (2) continuous sequencing, which means the reading of bases on a DNA strand is uninterrupted, and this characteristic can not only greatly increase a speed of sequencing, but greatly increase the read length of DNA.

Currently, based on this technology, Oxford Nanopore Technologies has launched commercial products such as MinION, GridION and PromethION. The supporting DNA library construction kit mainly adopts two approaches, 1D and 1D2. Since it is difficult to distinguish a signal of a single base by the nanopore sequencing and the differences in current signal caused by the four bases are very small, the sequencing has low accuracy when only relying on a single detection of the base and requires complex post-data analysis based on powerful hardware and software systems.

Based on the MinION platform of Oxford Nanopore Technologies, some companies currently have introduced 1D, 2D, and 1D2 library building approaches. However, all of these approaches have the disadvantages of insufficient accuracy and high sample initial volume. Some other related scientific research institutions have also successively developed methods for constructing libraries based on multiple copy numbers, including intramolecular-ligated nanopore consensus sequencing (INC-seq) (Li et al. GigaScience (2016) 5:34 DOI 10.1186/s13742-016-0140-7), rolling circle amplification multiplexed consensus sequencing method (R2C2), and self-amplification library construction method based on respiration (patent application No. 201610420179.5).

The existing construction method of nanopore sequencing library mainly employs the sequencing of a single copy number of base sequences. This method requires high sample initial volume and low accuracy, and set very high requirements for later data analysis. The conventional double strands constructed by multi-copy nanopore library are directly cyclized and Gibson-based assembly has a low efficiency, and generally the cyclized fragments are shorter than 1 kb, which limits the application of sequencing. The self-amplification method based on respiration requires relatively high Tm values at both ends, and there may be a phenomenon that the template DNAs are paired spontaneously during the amplification.

SUMMARY

The present disclosure provides a nanopore sequencing method. By constructing a multi-copy library that can be used for nanopore sequencing by a variety of methods, the signals of the long fragments can be repeatedly determined for multiple times, thereby effectively improving the accuracy of nanopore sequencing.

The present disclosure is embodied in the following technical solutions.

A nanopore sequencing method includes: in a nanopore sequencing device, performing a rolling circle amplification by using a single-stranded or double-stranded nucleic acid as a template nucleic acid to produce amplified single strands; under action of an electric field, introducing the amplified single strands into nanopores of the nanopore sequencing device in such a manner that the amplified single strands pass through the nanopores and generate an electrical signal for each base; and judging differences in the electrical signals caused by different bases to determine a base sequence of the template nucleic acid.

In a preferable embodiment, the template nucleic acid is a nucleic acid single-stranded loop; a reaction system of the rolling circle amplification includes the nucleic acid single-stranded loop, an amplification primer configured to partially hybridize with the nucleic acid single-stranded loop, as well as a polymerase having a strand displacement activity, dNTPs, and a reaction buffer; the method includes:
hybridizing the nucleic acid single-stranded loop with the amplification primer to form a hybrid product;
adding the hybrid product into the nanopore sequencing device, and adding the polymerase, dNTPs, and the reaction buffer to perform the rolling circle amplification to produce the amplified single strands; and
under action of the electric field, allowing each base of the amplified single strands to gradually pass through the nanopore and generate the electrical signal for each base, and judging the differences in the electrical signals caused by different bases to determine the base sequence of the template nucleic acid.

In a preferable embodiment, the reaction system further includes a probe sequence, the probe sequence includes a specific modification, the specific modification is connectable to a support layer supporting the nanopores in the nanopore sequencing device, and the amplification primer includes a probe recognition site capable of binding to the probe sequence; the method includes:
hybridizing the amplification primer and the probe sequence with the nucleic acid single-stranded loop to form the hybrid product;
adding the hybrid product into the nanopore sequencing device to connect the probe sequence to the support layer, and adding the polymerase, dNTPs and the reaction buffer to perform the rolling circle amplification to produce the amplified single strands; and
under action of the electric field, allowing each base of the amplified single strands to gradually pass through the nanopore and generate the electrical signal for each base, and judging the differences in the electrical signals caused by different bases to determine the base sequence of the template nucleic acid.

In a preferable embodiment, the reaction system further includes a probe sequence, the probe sequence includes a specific modification, the specific modification is connectable to a support layer supporting the nanopores in the nanopore sequencing device, and the amplification primer includes a probe recognition site capable of binding to the probe sequence; the method includes:
hybridizing the amplification primer with the nucleic acid single-stranded loop to form the hybrid product;

adding the probe sequence into the nanopore sequencing device to allow the probe sequence to be connected to the support layer, adding the hybrid product to hybridize the amplification primer with the probe sequence, and adding the polymerase, dNTPs and the reaction buffer to perform the rolling circle amplification to produce the amplified single strands; and under action of the electric field, allowing each base of the amplified single strands to gradually pass through the nanopore and generate the electrical signal for each base, and judging the differences in the electrical signals caused by different bases to determine the base sequence of the template nucleic acid.

In a preferable embodiment, the specific modification is selected from a cholesterol modification or a biotin modification.

In a preferable embodiment, the specific modification is the cholesterol modification, the support layer is a phospholipid bilayer, and cholesterol and the phospholipid bilayer are connected through affinity binding.

In a preferable embodiment, the specific modification is the biotin modification, the support layer includes a streptavidin modification, and biotin and streptavidin are connected through affinity binding.

In a preferable embodiment, the nucleic acid single-stranded loop includes a special modification, and the special modification is connectable to a support layer supporting the nanopores in the nanopore sequencing device; the method includes:

adding the amplification primer and the nucleic acid single-stranded loop into the nanopore sequencing device, to allow the amplification primer to hybridize with the nucleic acid single-stranded loop to form the hybrid product and to allow the nucleic acid single-stranded loop to be connected to the support layer through the special modification, and adding the polymerase, dNTPs and the reaction buffer to perform the rolling circle amplification to produce the amplified single strands; and under action of the electric field, allowing each base of the amplified single strands to gradually pass through the nanopore and generate the electrical signal for each base, and judging the differences in the electrical signals caused by different bases to determine the base sequence of the template nucleic acid.

In a preferable embodiment, the special modification is selected from biotin or polyethylene glycol.

In a preferable embodiment, the special modification is biotin, the support layer includes a streptavidin modification, and biotin and streptavidin are connected through affinity binding.

In a preferable embodiment, the template nucleic acid is a nucleic acid double-stranded loop; one strand of the nucleic acid double-stranded loop has a gap; a reaction system of the rolling circle amplification includes the nucleic acid double-stranded loop, as well as a polymerase having a strand displacement activity, dNTPs, and a reaction buffer; the method includes:

adding the nucleic acid double-stranded loop, the polymerase, dNTPs, and the reaction buffer into the nanopore sequencing device, and performing the rolling circle amplification to produce the amplified single strands from the one strand having the gap of the nucleic acid double-stranded loop; and under action of the electric field, allowing each base of the amplified single strands to gradually pass through the nanopore and generate the electrical signal for each base, and judging the differences in the electrical signals caused by different bases to determine the base sequence of the template nucleic acid.

In a preferable embodiment, the reaction system further includes a probe sequence, the probe sequence includes a specific modification, the specific modification is connectable to a support layer supporting the nanopores in the nanopore sequencing device, and the nucleic acid double-stranded loop includes a probe recognition site capable of binding to the probe sequence; the method includes:

adding the nucleic acid double-stranded loop, the probe sequence, the polymerase, dNTPs and the reaction buffer into the nanopore sequencing device, to allow the probe sequence to be connected to the support layer through the specific modification, and performing the rolling circle amplification to produce the amplified single strands from the one strand having the gap of the nucleic acid double-stranded loop; and under action of the electric field, allowing each base of the amplified single strands to gradually pass through the nanopore and generate the electrical signal for each base, and judging the differences in the electrical signals caused by different bases to determine the base sequence of the template nucleic acid.

In a preferable embodiment, the polymerase having a strand displacement activity is selected from phi29 polymerase or Bst polymerase.

In a preferable embodiment, a voltage of the electric field is a millivolt voltage.

In a preferable embodiment, the millivolt voltage is a voltage above 10 mV, preferably a voltage above 50 mV, more preferably a voltage ranging from 100 mV to 250 mV, and most preferably a voltage of 120 mV.

In a preferable embodiment, the method further includes a step of preparing the nucleic acid single-stranded loop or the nucleic acid double-stranded loop, and the step includes: cyclizing a DNA fragment to obtain a single-stranded loop or a double-stranded loop.

In a preferable embodiment, the DNA fragment has a length of 100 bp to 1 Mbp.

In a preferable embodiment, the nanopores are biological nanopores and solid-state nanopores.

In a preferable embodiment, the biological nanopores are protein nanopores, and a narrowest part of the protein nanopores allows a single-stranded nucleic acid to pass through.

In a preferable embodiment, the solid-state nanopores are nanopores of a silicon-based material or a graphene two-dimensional material, and a narrowest part of the nanopores of the silicon-based material allows a single-stranded nucleic acid to pass through.

The nanopore sequencing method of the present disclosure, which is based upon the preparation of a multi-copy DNA nanopore library, can not only remedy the problem of insufficient accuracy in the conventional nanopore sequencing library construction, but can also improve the efficiency of cyclization. In addition, the nanopore sequencing is performed while performing rolling circle amplification, such that the timeliness of sequencing can be improved, the time for library construction is shorted, and the sequencing steps are simplified. In the meantime, the present disclosure is compatible with all the base sequences that can be sequenced by the nanopore, without linker pollution and self-pairing phenomenon.

DESCRIPTION OF EMBODIMENTS

The present disclosure will be further described in detail through specific embodiments in conjunction with the drawings. In the following embodiments, many detailed descriptions are for the purpose of facilitating the understanding of the present disclosure. However, those skilled in the art can understand that some of the features can be omitted or replaced by other materials and methods under different circumstances.

In addition, features, operations, or features described in the specification can be combined in any appropriate manner to form various implementations. In the meantime, in a manner obvious to those skilled in the art, steps or actions for describing a method can also be exchanged or adjusted in terms of order. Therefore, the various orders in the specification and the drawings are only for the purpose of clearly describing a certain embodiment, but are not the necessary orders, unless it is otherwise stated that a certain order must be followed.

The present disclosure is mainly based on rolling circle amplification method to complete the construction and sequencing of a multi-copy library using nanopores. The present disclosure relates to a technical scheme for constructing a multi-copy library and the required oligonucleotide sequence composition, special modifications, reaction conditions, method steps and the like.

The basic principle of the present disclosure is, after the nucleic acid (such as DNA) to be tested is broken into long fragments, a single-stranded loop or a double-stranded loop is constructed by a specific method, and using the rolling circle amplification method and the nanopore sequencing device, under the action of electric field, the template nucleic acid to be tested can pass through the nanopore in a single-stranded form and generate electrical signals of different bases, by judging the differences in electrical signals caused by different bases, the template nucleic acids of different sequences can be identified.

In an embodiment of the present disclosure, a nanopore sequencing method includes: in a nanopore sequencing device, performing a rolling circle amplification by using a nucleic acid single-stranded loop or a nucleic acid double-stranded loop as a template nucleic acid to produce amplified single strands; under action of an electric field, introducing the amplified single strands into nanopores of the nanopore sequencing device in such a manner that the amplified single strands pass through the nanopores and generate an electrical signal for each base; and judging differences in the electrical signals caused by different bases to determine a base sequence of the template nucleic acid.

In the embodiments of the present disclosure, the nanopore sequencing device can be implemented as existing nanopore sequencing devices, for example, as a nanopore sequencing device disclosed in the International Application WO2014013262A1. The nanopore sequencing device can be a device based on biological nanopores or solid-state nanopores. The biological nanopores can be protein nanopores, and the solid-state nanopores can be nanopores of silicon-based material. The narrowest part of the nanopore allows a single-stranded nucleic acid to pass through. A support layer configured to support the nanopores can be a phospholipid bilayer (phospholipid membrane), a polymer membrane, or other supports with surface modification such as biotin modification.

In the embodiments of the present disclosure, the template nucleic acid includes two types, namely nucleic acid single-stranded loop and nucleic acid double-stranded loop, which can both be obtained by cyclizing a nucleic acid (such as DNA) fragment. Such a DNA fragment is a DNA sample used for library construction through cyclization, and a size of the fragment is generally a length suitable for constructing a single-stranded loop or a double-stranded loop, such as 100 bp to 1 Mbp. The nucleic acid (such as DNA) fragment may be derived from any biological samples of interest, such as animals, plants, microorganisms, etc. The nucleic acid single-stranded loop, such as a single-stranded DNA loop, is generally a closed DNA single-stranded loop (also referred as to a library) obtained by ligating a DNA fragment, as a template, with a designed linker and cyclizing the DNA fragment. The nucleic acid double-stranded loop, such as a double-stranded DNA loop, is generally a double-stranded circular DNA having a gap, which is obtained by ligating a DNA fragment, as a template, with a specially designed linker and then performing other appropriate technical solutions.

Figure 1:
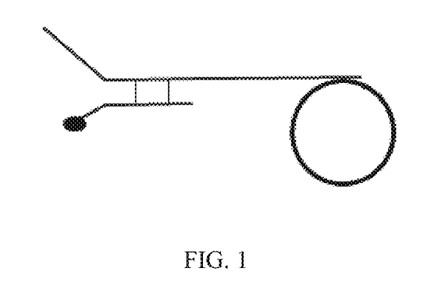
FIG. 1 is a schematic structural diagram of a DNA linker sequence used in a construction of a library according to an embodiment of the present disclosure.

As illustrated in FIG. 1, in an embodiment of the present disclosure, a DNA linker sequence is used for library construction, and the DNA linker sequence is composed of two base sequences of different lengths. As illustrated in FIG. 1, the longer base sequence has a fragment of sequence that can specifically bind to a single-stranded loop at an extension of 3'-terminal. The DNA linker sequence has a specific modified base sequence on one strand, such as a modification at the 3'-terminal of the short strand shown in FIG. 1, for example, cholesterol or biotin modification. This specific modification can be connected to the support layer configured to support the nanopores in the nanopore sequencing device, so as to immobilize the entire DNA linker sequence on the support layer.

It should be noted that, in the embodiments of the present disclosure, when the template nucleic acid is a nucleic acid single-stranded loop, the linker sequence essential for nanopore sequencing is the sequence shown in FIG. 1 that has a fragment of sequence capable of specifically binding to a single-stranded loop, this sequence serves as a primer for rolling circle amplification, and thus this sequence is also referred as to an "amplification primer" in the present disclosure. The short strand having a modification at the 3'-terminal, as shown in FIG. 1, serves as a preferred sequence for connecting to the support layer of the nanopores, such that the amplified single strand is close to the nanopore and enters the nanopore. In the present disclosure, the short strand is also referred as to a "probe sequence".

When the template nucleic acid is the nucleic acid single-stranded loop, a reaction system of the rolling circle amplification in the nanopore sequencing method according to the present disclosure includes the following components: a nucleic acid single-stranded loop, an amplification primer configured to partially hybridize with the nucleic acid single-stranded loop, as well as a polymerase having a strand displacement activity, dNTPs, and a reaction buffer. The nanopore sequencing method of the present disclosure includes: hybridizing the nucleic acid single-stranded loop with the amplification primer to form a hybrid product; adding the hybrid product into the nanopore sequencing device, and adding the polymerase, dNTPs, and the reaction buffer to perform the rolling circle amplification to produce the amplified single strands; and under action of the electric field, allowing each base of the amplified single strand to gradually pass through the nanopore and generate the electrical signal for each base, and judging the differences in the electrical signals caused by different bases to determine the base sequence of the template nucleic acid.

Figure 2:
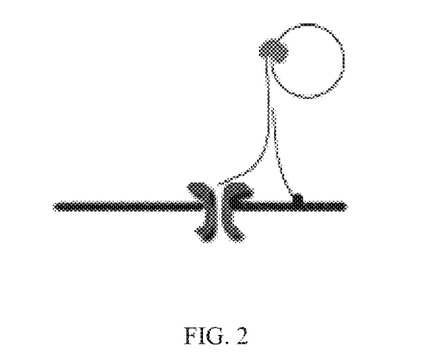
FIG. 2 is a schematic diagram of a method for sequencing by hybridizing single-stranded DNA loop with a linker and then placing in a nanopore device according to an embodiment of the present disclosure.

In a preferable embodiment, a single-stranded DNA loop-based nanopore multi-copy library construction and sequencing method, as illustrated in FIG. 2, is a method for sequencing in which a single-stranded DNA loop is hybridized with a linker (including long and short strands) and then placed in the nanopore device. A reaction system includes a nucleic acid single-stranded loop, an amplification primer (i.e., the long strand) configured to partially hybridize with the nucleic acid single-stranded loop, a probe sequence (i.e., the short strand), as well as a polymerase having a strand displacement activity, dNTPs, and a reaction buffer. The probe sequence has a specific modification, such as a cholesterol or biotin modification, and the specific modification is connectable to the support layer supporting the nanopores in the nanopore sequencing device. The amplification primer includes a probe recognition site capable of binding to the probe sequence. The method includes: hybridizing the amplification primer and the probe sequence with the nucleic acid single-stranded loop to form the hybrid product; adding the hybrid product into the nanopore sequencing device to connect the probe sequence to the support layer, and adding the polymerase, dNTPs and the reaction buffer to perform the rolling circle amplification to produce the amplified single strands; and under action of the electric field, allowing each base of the amplified single strands to gradually pass through the nanopore and generate the electrical signal for each base, and judging the differences in the electrical signals caused by different bases to determine the base sequence of the template nucleic acid.

In a specific embodiment, the amplification primer (i.e., the long strand) and the probe sequence (i.e., the short strand) both have partial sequence complementarity. The 3'-terminal of the short strand is modified, for example, with a cholesterol or biotin modification, etc., and the hybrid product is hybridized with the short strand. Then, the hybrid product is placed into a sequencing device formed with nanopores, and the modification at the 3'-terminal of the short strand can interact with the surface of the support layer to be adsorbed on the surface, allowing an enrichment of the hybrid product on the surface of the nanopore. By adding the polymerase and dNTPs to the sequencing device as well as applying an electric field to the entire sequencing device, the 5'-terminal of the long strand of the linker sequence enters the nanopore, and thus a single base can gradually pass through the nanopore under the action of the polymerase and the electric field, the generated current signal is recorded.

Figure 3:
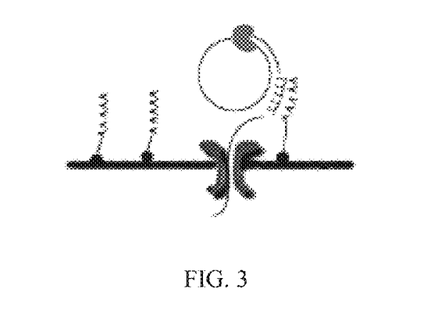
FIG. 3 is a schematic diagram of a method for sequencing by hybridizing a single-stranded DNA loop with a surface-immobilized sequence in a nanopore system according to an embodiment of the present disclosure.

In a preferable embodiment, a single-stranded DNA loop-based nanopore multi-copy library construction and sequencing method, as illustrated in FIG. 3, shows a hybridization of a single-stranded DNA loop with a surface-immobilized sequence in a nanopore system. The reaction system includes a nucleic acid single-stranded loop, an amplification primer (i.e., the long strand) configured to partially hybridize with the nucleic acid single-stranded loop, a probe sequence (i.e., the short strand), as well as a polymerase having a strand displacement activity, dNTPs, and a reaction buffer. The probe sequence has a specific modification, such as a cholesterol or biotin modification, and the specific modification is connectable to the support layer supporting the nanopores in the nanopore sequencing device. The amplification primer includes a probe recognition site capable of binding to the probe sequence. The method includes: hybridizing the amplification primer with the nucleic acid single-stranded loop to form the hybrid product; adding the probe sequence into the nanopore sequencing device to allow the probe sequence to be connected to the support layer, adding the hybrid product to hybridize the amplification primer with the probe sequence, and adding the polymerase, dNTPs and the reaction buffer to perform the rolling circle amplification to produce the amplified single strands; and under action of the electric field, allowing each base of the amplified single strands to gradually pass through the nanopore and generate the electrical signal for each base, and judging the differences in the electrical signals caused by different bases to determine the base sequence of the template nucleic acid.

In a specific embodiment, two oligonucleotide sequences (oligos) are designed, one of which is a short strand having a modification (such as cholesterol, biotin, etc.) at the 3'-terminal, referred to as the probe sequence; and the other one of which is a long strand having a probe recognition site and capable of hybridizing with the DNA single-stranded loop, referred as to the amplification primer. The amplification primer is hybridized with the DNA single-stranded loop to form a primer-single-stranded DNA (primer-ssDNA) hybrid product. The short strand having the modification at the 3'-terminal, i.e., the probe sequence, is immobilized on a surface of the support layer to form a high-density of probe sequences on the surface of the support layer. Then, the primer-ssDNA hybrid product is added into the sequencing device formed with the nanopores, so as to hybridize the probe recognition site on the hybrid product with the probe sequence on the surface of the support layer. The polymerase and dNTPs are added into the nanopore sequencing device, and a voltage is applied across the nanopore. The 5'-terminal of the long strand (the amplification primer) can enter the nanopore under the action of the electric field, and each base can pass through the nanopore under the action of the polymerase and generate a corresponding current signal.

In the above embodiment, the modification on the short strand may be a cholesterol modification, the support layer may be a phospholipid bilayer, and the cholesterol and the phospholipid bilayer are connected by affinity binding. In other embodiments, the modification on the short strand may be a biotin modification, the support layer has a streptavidin modification, and the biotin and streptavidin are connected through affinity binding.

Figure 4:
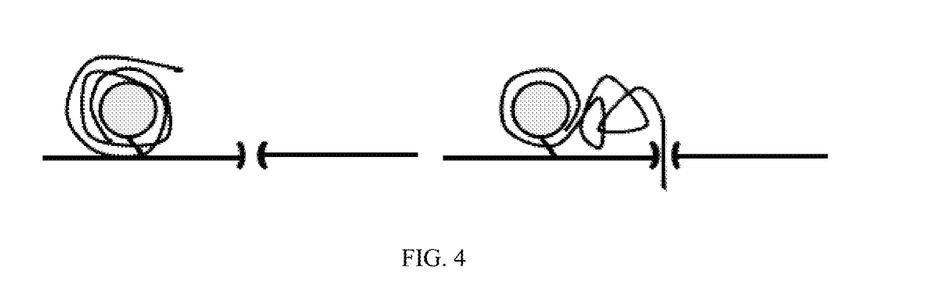
FIG. 4 is a schematic diagram of a method for sequencing by immobilizing a single-stranded DNA loop with a special modification on a support layer according to an embodiment of the present disclosure.

In a preferable embodiment, a single-stranded DNA loop-based nanopore multi-copy library construction and sequencing method, as illustrated in FIG. 4, shows a method for sequencing, in which a single-stranded DNA loop is subjected to a special modification to be immobilized on the surface of the support layer. The reaction system includes a nucleic acid single-stranded loop, an amplification primer (i.e., the long strand) configured to partially hybridize with the nucleic acid single-stranded loop, as well as a polymerase having a strand displacement activity, dNTPs, and a reaction buffer. The nucleic acid single-stranded loop has a special modification, such as biotin or polyethylene glycol, and the specific modification is connectable to the support layer supporting the said nanopore in the nanopore sequencing device. The amplification primer includes a probe recognition site capable of binding to the probe sequence. The method includes: adding the amplification primer and the nucleic acid single-stranded loop into the nanopore sequencing device, to allow the amplification primer to hybridize with the nucleic acid single-stranded loop to form the hybrid product and to allow the nucleic acid single-stranded loop to be connected to the support layer through the special modification, and adding the polymerase, dNTPs and the reaction buffer to perform the rolling circle amplification to produce the amplified single strands; and under action of the electric field, allowing each base of the amplified single strands to gradually pass through the nanopore and generate the electrical signal for each base, and judging the differences in the electrical signals caused by different bases to determine the base sequence of the template nucleic acid.

In a specific embodiment, a specific base on the nucleic acid single-stranded loop is label-modified, and the label-modification can be biotin or other similar chemical substances such as polyethylene glycol. The base with the labeled modification needs to be modified. The base with the label-modification must have normal polymerization function, but cannot be replaced from the bilayer surface under the action of polymerase. After the reaction starts, the single-stranded DNA amplified by the rolling circle amplification passes through the nanopore under the action of an electric field and generates a corresponding electrical signal.

In the above embodiment, the special modification may be biotin, and the support layer has a streptavidin modification, and the biotin and streptavidin are connected through affinity binding.

Figure 5:
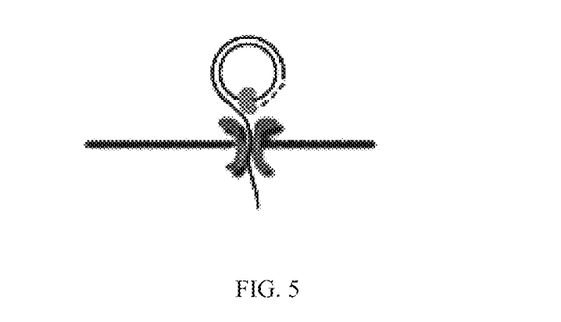
FIG. 5 is a schematic diagram of a method for constructing and sequencing a DNA double-stranded loop library without a probe recognition site according to an embodiment of the present disclosure.

In a preferable embodiment, a double-stranded DNA loop-based nanopore multi-copy library construction and sequencing method, as illustrated in FIG. 5, shows a construction and sequencing method of a DNA double-stranded loop library without a probe recognition site. In this method, the template nucleic acid is a nucleic acid double-stranded loop, and one strand of the nucleic acid double-stranded loop has a gap. The reaction system includes: a nucleic acid double-stranded loop, as well as a polymerase having a strand displacement activity, dNTPs, and a reaction buffer. The method includes: adding the nucleic acid double-stranded loop, the polymerase, dNTPs, and the reaction buffer into the nanopore sequencing device, and performing the rolling circle amplification to produce the amplified single strands from the one strand having the gap of the nucleic acid double-stranded loop; and under action of the electric field, allowing each base of the amplified single strands to gradually pass through the nanopore and generate the electrical signal for each base, and judging the differences in the electrical signals caused by different bases to determine the base sequence of the template nucleic acid.

In the embodiments of the present disclosure, the nucleic acid double-stranded loop including one strand with a gap can be prepared by the existing conventional method. For example, in one embodiment, the DNA double-stranded loop is prepared as follows: a terminal of a DNA fragment is paired and added with an A-tailing; a specially designed linker (for example, two fragments of the linker are asymmetrical, one of which is longer, and the other one is shorter, i.e., a linker having a bifurcation structure) is added; a specially designed primer is used for PCR amplification; a User enzyme is adopted for processing to obtain the double-stranded DNA having complementary sequences at both terminals; cyclization treatment is performed to form the double-stranded DNA loop having a gap during the cyclization due to the presence of the specially designed primer.

Figure 6:
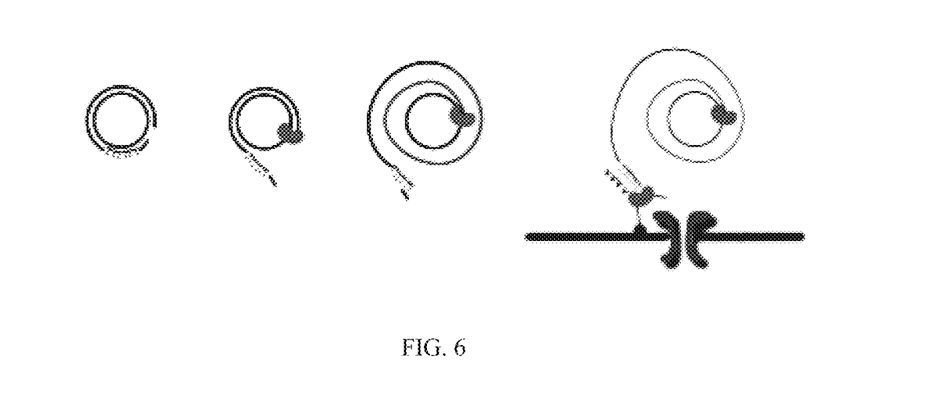
FIG. 6 is a schematic diagram of a method for constructing and sequencing a DNA double-stranded loop library with a probe recognition site according to an embodiment of the present disclosure.

In a preferable embodiment, a double-stranded DNA loop-based nanopore multi-copy library construction and sequencing method, as illustrated in FIG. 6, shows a construction and sequencing method of a DNA double-stranded loop library with a probe recognition site. In this method, the template nucleic acid is a nucleic acid double-stranded loop, and one strand of the nucleic acid double-stranded loop has a gap. The reaction system includes: a nucleic acid double-stranded loop, a polymerase having a strand displacement activity, dNTPs, a reaction buffer, and a probe sequence. The probe sequence has a specific modification, and the specific modification is connectable to a support layer supporting the nanopores in the nanopore sequencing device. The nucleic acid double-stranded loop includes a probe recognition site capable of binding to the probe sequence. The method includes: adding the nucleic acid double-stranded loop, the probe sequence, the polymerase, dNTPs and the reaction buffer into the nanopore sequencing device, to allow the probe sequence to be connected to the support layer through the specific modification, and performing the rolling circle amplification to produce the amplified single strands from the one strand having the gap of the nucleic acid double-stranded loop; and under action of the electric field, allowing each base of the amplified single strands to gradually pass through the nanopore and generate the electrical signal for each base, and judging the differences in the electrical signals caused by different bases to determine the base sequence of the template nucleic acid.

In the embodiments of the present disclosure, the polymerase having a strand displacement activity is selected from phi29 polymerase or Bst polymerase. A voltage of the electric field is a millivolt voltage, for example, a voltage above 10 mV, preferably a voltage above 50 mV, more preferably a voltage ranging from 100 mV to 250 mV, and most preferably a voltage of 120 mV.

The technical solutions of the present disclosure are described in detail below through examples. It should be understood that the examples are merely illustrative and should not be understood as limitations to the protection scope of the present disclosure.

Example 1

Preparation of Single-Stranded Circular DNA

Using the MGIEasy™ DNA library preparation kit (BGI, Shenzhen), DNA was extracted from raw materials, standard strains of *Escherichia coli*, and the single-stranded circular DNA was prepared according to the kit instruction.

Example 2

Preparation of Double-Stranded Circular DNA 1. phiX174 Plasmid Linearization

1 μg of phiX174 (1 μL, NEB Inc.) was taken and added with 1 μL of ssPI enzyme (NEB Inc.) and 5 μL of 10× Smart buffer, and then added with 43 μL of water up to a volume of 50 μL. After vortex mixing, the mixture was placed into a PCR amplifier. The reaction procedure was as follows: reacting at 37° C. for 30 minutes, reacting at 65° C. for 20 minutes, and storing at 4° C.

2. Addition of A-Tailing to Linearized DNA

20 μL of linearized phiX174 was taken and added with 3 μL of 10×NEB buffer 2 (NEB Inc.), 0.075 μL of 100 mM dATP (Enzymatics) and 6 U of Klenow Exo- (Enzymatics), and added with water up to a volume of 30 μL. After vortex mixing, the mixture was placed into a PCR amplifier. The reaction procedure was as follows: reacting at 37° C. for 30 minutes and storing at 4° C.

3. Addition of Linker and Ligation

YJ-1058 and YJ-1092 sequences in Table 1 were hybridized to obtain 25 μM of hybridized linker product, 13 μL of the product was taken and added with 1.6 μL of linker (25 μM) and 0.55 μL of T4 DNA ligase (BGI, 600 U/μL), and then added with water up to a volume of 30 μL. After vortex mixing, the mixture was placed into a PCR amplifier. The reaction procedure was as follows: reacting at 20° C. for 30 minutes and storing at 4° C. 0.5× AM Xpure magnetic beads were used for purification, and dissolved with 60 μL of TE.

4. PCR of Ligation Product 320 ng of the above product was taken and added with 10 U of Pfu Curbo Tur (Promega), 100 μL of PfuCx mix3 (Promega), 1.6 μL of dNTP (Enzymatics, 25 mM), 5 μL of YJ-1054 primer (20 μM, Table 1) and 5 μL of YJ-1055 primer (20 μM, Table 1), and then added with water up to a volume of 200 μL. After mixing, the following reaction program was adopted: 95° C. for 3 min; 9 cycles at 92° C., 30 secs+56° C., 30 secs+72° C., 20 min, 68° C., 18 min, and cooling to 4° C. within 0.1 second.

5. Treatment of PCR Product with User Enzyme 4.5 μg PCR product was taken and added with 11 μL of 10× Taq buffer (NEB Inc.) and 12 μL of User enzyme (NEB Inc.), and then added with water up to 110 μL. After mixing, the mixture reacted in a PCR amplifier for 60 min, then added with 180 μL of TA buffer (BGI), and added with water up to a volume of 1810 μL, then reacted in a water bath at 70° C. for 30 minutes and cooled at room temperature for 20 minutes.

6. Cyclization

200 μL of 10× smart buffer and 2 μL of T4 DNA ligase (NEB Inc.) were added to the above product, then water was added up to a volume of 2 ml. The mixture reacted at room temperature for 2 hours, a mixture of 0.5× AM Xpure magnetic beads and HBB (1:1) was used for purification, and dissolved with 60 μL of TE.

7. Digestion of Uncyclized Product 59.1 μL of the cyclization product was taken and added with 8.9 μL of 9× PS mix, 9 μL of Plasmid-Safe enzyme, and 3 μL of ATP. After mixing, the mixture was placed in the PCR amplifier and reacted at 37° C. for 1 hour. 1× AM Xpure magnetic beads were used for purification, and dissolved with 60 μL of TE.

8. Treatment with Polymerase I

10 μL of the above purified product was taken and added with 1 μL of polymerase I, 9 μL of NEBuffer 2. After mixing, the mixture was placed and reacted in the PCR amplifier, with a reaction procedure of reacting at 14° C. for 30 min.

Figure 7:
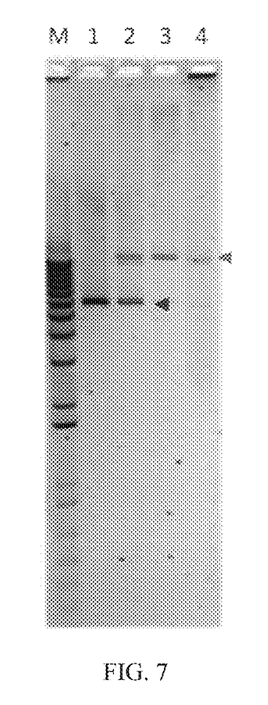
FIG. 7 is a diagram showing the result of agarose gel electrophoresis of double-stranded circular DNA prepared in an embodiment of the present disclosure.

9. Agarose Gel Electrophoresis 20 ng of PCR product, 20 ng of the cyclization product, 20 ng of the digested cyclization product, and 20 ng of the polymerase I-treated product were taken and tested with gel electrophoresis using 0.8% gel, respectively. The results are shown in FIG. 7.

Track M is 1 kb plus ladder. Track 1 is the PCR product, and the triangle corresponds to a band of linear phiX174. Track 2 is the cyclization product, the lower triangle corresponds to a band of linear phiX174 band, and the upper triangle corresponds to the cyclized double-stranded DNA loop. Track 3 is the cyclization product digested with Plasmid-safe enzyme, and the triangle corresponds to the cyclized double-stranded DNA loop. Track 4 is a band of the product obtained by digesting the cyclization product with Plasmid-safe enzyme and then treating with polymerase I, and the triangle corresponds to the cyclized double-stranded DNA loop. By comparing tracks 1 and 2, it can be seen that the cyclization efficiency was close to 30%; the comparison of tracks 2 and 3 indicates that the upper triangle corresponds to a double-stranded loop; the comparison of tracks 3 and 4 indicates that the formed double-stranded loop contains a complete closed loop.

[TABLE 1]

| Primer name | Primer sequence |
|---|---|
| YJ-1092 | 5phos/AGTCGGAGGCCAAGCG GTCTTAGGAAGACAATAGGTCC GATCAACTCCTTGGCTCACAGA ACGACAT (SEQ ID NO: 1) |
| YJ-1058 | CTTGGCUCACAGAACGACAUGG CTACGATCCGACTT (SEQ ID NO: 2) |
| YJ-1054 | CTTGGCUCACAGAACGACAUGG CTAC (SEQ ID NO: 3) |
| YJ-1055 | ATGTCGTTCTGUGAGCCAAGGA GUTG (SEQ ID NO: 4) |

Example 3

Rolling Circle Amplification of Double-Stranded Circular DNA

The cyclized double-stranded DNA library, 2× phi29 buffer (Enzymatics), phi29 enzyme (Enzymatics), 100 mM EDTA at pH8.0 (Invitrogen) were placed on the ice box for about 0.5 h and thawed, then shook and mixed using a vortex shaker for 5 seconds, and centrifuged briefly and then placed on an ice box for later use.

1. Adding 20 μL of double-stranded DNA loop in a concentration of 40 fmol.

2. Adding 20 μL of 2× phi29 buffer to a PCR tube, mixing and placing in a PCR amplifier, incubating at 30° C. for 5 minutes.

3. Adding 40 μL of 2× phi29, 4 μL of phi29 enzyme (Enzymatics) into each reaction tube, mixing with a pipette tip, and placing in a PCR amplifier under the reaction condition of 30° C. for 2 hours.

4. When the reaction was complete, adding 20 µL of EDTA (100 mM, pH 8.0) to each reaction tube and mixing.

Figure 8:
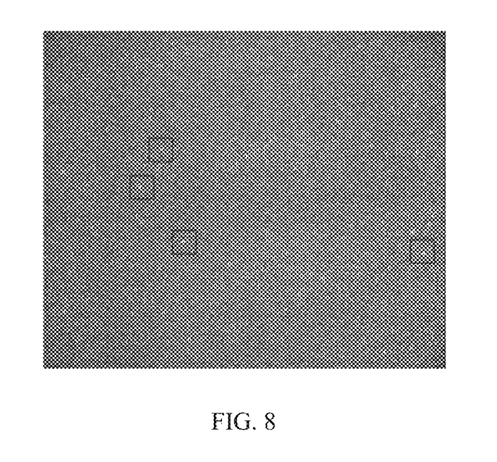
FIG. 8 is a diagram showing the result of a forward sequencing of DNA nanospheres obtained by rolling circle amplification of double-stranded circular DNA in an embodiment of the present disclosure.

5. Using a BGISEQ-500 sequencing kit, loading a sequencing chip on a BGISEQ-500 sequencer according to the kit instructions, and loading the above-mentioned reaction product, DNA nanoballs (DNBs), on the BGISEQ-500 platform; performing sequencing according to the sequencing kit instructions, setting the parameters to take pictures. The results of the first round of forward sequencing are shown in FIG. 8. FIG. 8 illustrates the results of one cycle of forward sequencing on the BGISEQ-500 platform, where the bright spot indicates multiple copies of DNB, and the box indicates the position of the DNB.

The results of this example indicates that the double-stranded DNA library can be prepared and subjected to rolling circle amplification for sequencing.

Example 4

Nanopore Sequencing Based on Single-Stranded Loop

1. Two oligonucleotide sequences (oligos) were designed, one of which is a short strand having a modification (cholesterol) at the 3'-terminal, as a probe sequence (SEQ ID NO: 5: CCGCGTGAGATCTGATGATGTTTTTAAAT-TTGGGTTT/iSpC3/-Cholesterol, where /iSpC3/ represents —CH2CH2CH2— for block the polymerization of DNA, Cholesterol refers to cholesterol); and the other one of which is a long strand having a probe recognition site and capable of hybridizing with the DNA single-stranded loop (SEQ ID NO: 6: /iSpC3/AAAAAAACCTTCC/iSpC3/CCTTCCCAT-CATCATCAGATCTCACGCG-GAAAAAAAAAAAAAAAAAAAAAAAA/iSpC3//iSpC3//iSpC3//iSpC3//iSpC3//iSpC3//iSpC3/GAACGACATGGCTACGA, where the underlined part of the sequence is complementary to the circular DNA, /iSpC3//iSpC3//iSpC3//iSpC3//iSpC3//iSpC3//iSpC3/ is for purpose of recognition, when a current signal thereon is detected, it means that the detection of the sequence under test begins). The long-strand sequence was hybridized with the single-stranded circular DNA in Example 1 to form a primer-single-stranded DNA (primer-ssDNA) hybrid product.

2. Building a nanopore test device: Axopatch 200B Patch Clam (Axon) and data acquisition board 1550A (Axon) were used to build a signal acquisition platform, and a groove having 100 µM pores (warner, BCH-M13) was used for nanopore experiment and film formation experiment.

Figure 9:
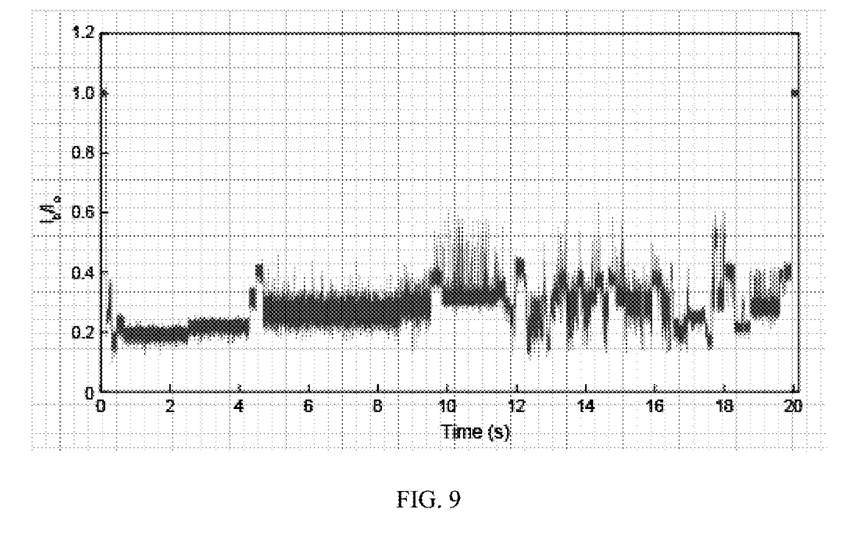
FIG. 9 is a current change graph obtained by performing a nanopore sequencing on a single-stranded loop in an embodiment of the present disclosure.

3. 1 mL of KCl solution (300 mM) was added to each of the tanks on both sides of the groove for experiment, a voltage of 120 mV was applied to the other side of the groove (trans) to form a bilayer phospholipid membrane, and MspA protein was added to form a protein nanopore. In the one side of the groove (cis), 5 µL of primer-ssDNA hybrid product (10 µM) was added to a cis end, 10 µL of wild-type (WT) phi29 polymerase (10 mg/ml) and 10 µL of dNTP (Enzymatics, 25 mM) were added and reacted at room temperature, the current changes were recorded, as shown in FIG. 9.

Example 5

Nanopore Sequencing Based on Double-Stranded Loop 1. 1 µg of phiX174 (1 µL, NEB Inc.) was taken and added with 1 µL of ssPI enzyme (NEB Inc.) and 5 µL of 10× Smart buffer, and then added with 43 µL of water up to a volume of 50 µL. After vortex mixing, the mixture was placed into a PCR amplifier. The reaction procedure was as follows: reacting at 37° C. for 30 minutes, reacting at 65° C. for 20 minutes, and storing at 4° C.

2. GL-25 and GL-26 sequences in Table 2 were hybridized to obtain a 25 µM hybridized linker product, 13 µL of the above product was taken and added with 1.6 µL of linker (25 µM), 9 µL of 3× HB buffer (BGI), 0.55 µL of T4 DNA ligase (BGI, 600 U/µL), and then added with water up to a volume of 30 µL. After vortex mixing, the mixture was placed into a PCR amplifier. The reaction procedure was as follows: reacting at 20° C. for 30 minutes and storing at 4° C. 0.5× AM Xpure magnetic beads were used for purification, and dissolved with 60 µL of TE.

3. PCR of Ligation Product 320 ng of the above product was taken and added with 10 U of Pfu Curbo Tur (Promega), 100 µL of PfuCx mix3 (Promega), 1.6 µL of dNTP (Enzymatics, 25 mM), 5 µL of YJ-1054 primer (20 µM, Table 2) and 5 µL of YJ-1055 primer (20 µM, Table 2), and then added with water up to a volume of 200 µL. After mixing, the following reaction program was adopted: 95° C. for 3 min; 9 cycles at 92° C., 30 secs+56° C., 30 secs+72° C., 20 min, 68° C., 18 min, and cooling to 4° C. within 0.1 second.

4. Treatment of PCR Product with User Enzyme 4.5 µg PCR product was taken and added with 11 µL of 10× Taq buffer (NEB Inc.) and 12 µL of User enzyme (NEB Inc.), and then added with water up to 110 µL. After mixing, the mixture reacted in a PCR amplifier for 60 min, then added with 180 µL of TA buffer (BGI), and added with water up to a volume of 1810 µL, then reacted in a water bath at 70° C. for 30 minutes and cooled at room temperature for 20 minutes.

5. Cyclization

200 µL of 10× smart buffer and 2 µL of T4 DNA ligase (NEB Inc.) were added to the above product, then water was added up to a volume of 2 ml. The mixture reacted at room temperature for 2 hours, a mixture of 0.5× AM Xpure magnetic beads and HBB (1:1) was used for purification, and dissolved with 60 µL of TE.

6. Digestion of Uncyclized Product 59.1 µL of the cyclization product was taken and added with 8.9 µL of 9× PS mix, 9 µL of Plasmid-Safe enzyme, and 3 µL of ATP. After mixing, the mixture was placed in the PCR amplifier and reacted at 37° C. for 1 hour. 1× AM Xpure magnetic beads were used for purification, and dissolved with 60 µL of TE, a concentration thereof was 20 ng/µL.

7. Building a nanopore test device: Axopatch 200B Patch Clam (Axon) and data acquisition board 1550A (Axon) were used to build a signal acquisition platform, and a groove having 100 µM pores (warner, BCH-M13) was used for nanopore experiment and film formation experiment.

8. 1 mL of KCl solution (300 mM) was added to each of the tanks on both sides of the groove for experiment, 5 µL of oligonucleotide sequence (10 µM, SEQ ID NO: 7: AAAAAAAAAAAAAAAAA-chelesetrol) was added to one side of the groove (cis), and a voltage of 120 mV was applied to the other side of the groove (trans), a bilayer phospholipid membrane was formed by a lifting method, and MspA protein was added to form a protein nanopore.

Figure 10:
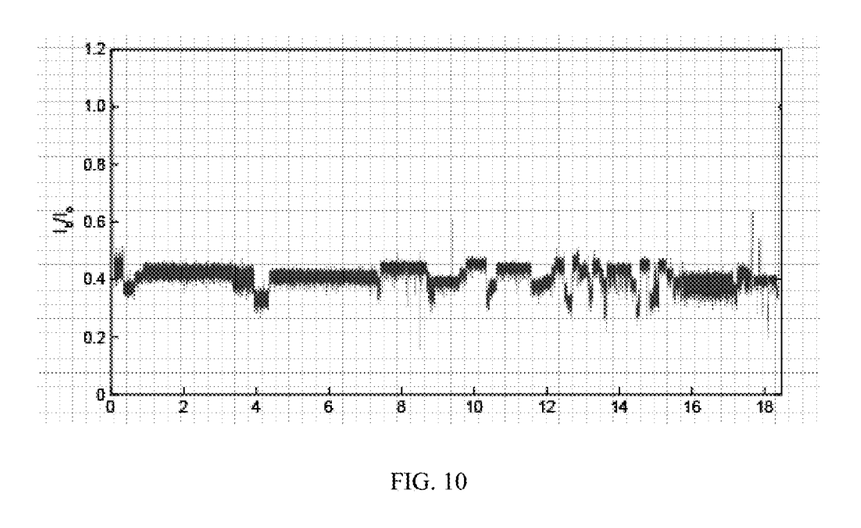
FIG. 10 is a current change graph obtained by performing a nanopore sequencing on a double-stranded loop in an embodiment of the present disclosure.

9. 400 ng of the purified double-stranded loop was added to the cis end, and 10 µL of wild-type phi29 polymerase (10 mg/ml) and 10 µL of dNTP (Enzymatics, 25 mM) were added and reacted at room temperature, the current changes were recorded, as shown in FIG. 10.

[TABLE 2]

| Primer name | Primer sequence |
| --- | --- |
| GL-25 | 5phos/AGTCGGAGGCCAAG CGGTCTTAGGAAGACAATAG GTCCGATTTTTTTTTTTTT TTTTTTTCAACTCCTTGGCT CACAGAACGACAT (SEQ ID NO: 8) |
| GL-26 | CTTGGCUCACAGAACGACAU GGCTACGATCCGACTT (SEQ ID NO: 9) |
| YJ-1054 | CTTGGCUCACAGAACGACAU GGCTAC (SEQ ID NO: 10) |

[TABLE 2]-continued

| Primer name | Primer sequence |
| --- | --- |
| YJ-1055 | ATGTCGTTCTGUGAGCCAAG GAGUTG (SEQ ID NO: 11) |

The present disclosure is explained with the above specific examples, which are merely intended to facilitate the understanding of the present disclosure, but not to limit the present disclosure. Those skilled in the art to which the present disclosure belongs, based on the concept of the present disclosure, can make several easier deductions, modifications or substitutions.

What is claimed is:

1. A nanopore sequencing method, comprising: in a nanopore sequencing device, performing a rolling circle amplification by using a single-stranded or double-stranded nucleic acid as a template nucleic acid to produce amplified single strands; under action of an electric field, introducing the amplified single strands into nanopores of the nanopore sequencing device in such a manner that the amplified single strands pass through the nanopores and generate an electrical signal for each base; and judging differences in the electrical signals caused by different bases to determine a base sequence of the template nucleic acid, wherein:

when the template nucleic acid is a single-stranded nucleic acid loop, the reaction system further comprises a probe sequence, the probe sequence comprises a specific modification, the specific modification is connectable to a support layer supporting the nanopores in the nanopore sequencing device, and the amplification primer comprises a probe recognition site capable of binding to the probe sequence; or when the template nucleic acid is a double-stranded nucleic acid loop, the reaction system further comprises a probe sequence, the probe sequence comprises a specific modification, the specific modification is connectable to a support layer supporting the nanopores in the nanopore sequencing device, and the nucleic acid double-stranded loop comprises a probe recognition site capable of binding to the probe sequence.

2. The nanopore sequencing method according to claim 1, wherein the template nucleic acid is a nucleic acid single-stranded loop; a reaction system of the rolling circle amplification comprises the nucleic acid single-stranded loop, an amplification primer configured to partially hybridize with the nucleic acid single-stranded loop, as well as a polymerase having a strand displacement activity, dNTPs, and a reaction buffer; and the method comprises:

hybridizing the nucleic acid single-stranded loop with the amplification primer to form a hybrid product;

adding the hybrid product into the nanopore sequencing device, and adding the polymerase, dNTPs, and the reaction buffer to perform the rolling circle amplification to produce the amplified single strands; and under action of the electric field, allowing each base of the amplified single strand to gradually pass through the nanopore and generate the electrical signal for each base, and judging the differences in the electrical signals caused by different bases to determine the base sequence of the template nucleic acid.

3. The nanopore sequencing method according to claim 2, the method comprises:

hybridizing the amplification primer and the probe sequence with the nucleic acid single-stranded loop to form the hybrid product;

adding the hybrid product into the nanopore sequencing device to connect the probe sequence to the support layer, and adding the polymerase, dNTPs and the reaction buffer to perform the rolling circle amplification to produce the amplified single strands; and under action of the electric field, allowing each base of the amplified single strands to gradually pass through the nanopore and generate the electrical signal for each base, and judging the differences in the electrical signals caused by different bases to determine the base sequence of the template nucleic acid.

4. The nanopore sequencing method according to claim 2, the method comprises:
hybridizing the amplification primer with the nucleic acid single-stranded loop to form the hybrid product;
adding the probe sequence into the nanopore sequencing device to allow the probe sequence to be connected to the support layer, adding the hybrid product to hybridize the amplification primer with the probe sequence, and adding the polymerase, dNTPs and the reaction buffer to perform the rolling circle amplification to produce the amplified single strands; and
under action of the electric field, allowing each base of the amplified single strands to gradually pass through the nanopore and generate the electrical signal for each base, and judging the differences in the electrical signals caused by different bases to determine the base sequence of the template nucleic acid.

5. The nanopore sequencing method according to claim 3, wherein the specific modification is selected from a cholesterol modification or a biotin modification;
when the specific modification is the cholesterol modification, the support layer is a phospholipid bilayer, and cholesterol and the phospholipid bilayer are connected through affinity binding; and
when the specific modification is the biotin modification, the support layer comprises a streptavidin modification, and biotin and streptavidin are connected through affinity binding.

6. A nanopore sequencing method, comprising: in a nanopore sequencing device, performing a rolling circle amplification by using a single-stranded or double-stranded nucleic acid as a template nucleic acid to produce amplified single strands; under action of an electric field, introducing the amplified single strands into nanopores of the nanopore sequencing device in such a manner that the amplified single strands pass through the nanopores and generate an electrical signal for each base; and judging differences in the electrical signals caused by different bases to determine a base sequence of the template nucleic acid,
wherein the nucleic acid single-stranded loop comprises a special modification, and the special modification is connectable to a support layer supporting the nanopores in the nanopore sequencing device; and the method comprises:
adding the amplification primer and the nucleic acid single-stranded loop into the nanopore sequencing device, to allow the amplification primer to hybridize with the nucleic acid single-stranded loop to form the hybrid product and to allow the nucleic acid single-stranded loop to be connected to the support layer through the special modification, and adding the polymerase, dNTPs and the reaction buffer to perform the rolling circle amplification to produce the amplified single strands; and
under action of the electric field, allowing each base of the amplified single strands to gradually pass through the nanopore and generate the electrical signal for each base, and judging the differences in the electrical signals caused by different bases to determine the base sequence of the template nucleic acid.

7. The nanopore sequencing method according to claim 6, wherein the special modification is selected from biotin or polyethylene glycol.

8. The nanopore sequencing method according to claim 7, wherein the special modification is biotin, the support layer comprises a streptavidin modification, and biotin and streptavidin are connected through affinity binding.

9. The nanopore sequencing method according to claim 1, wherein when the template nucleic acid is a nucleic acid double-stranded loop, the method comprises:
adding the nucleic acid double-stranded loop, the probe sequence, the polymerase, dNTPs and the reaction buffer into the nanopore sequencing device, to allow the probe sequence to be connected to the support layer through the specific modification, and performing the rolling circle amplification to produce the amplified single strands from the one strand having the gap of the nucleic acid double-stranded loop; and
under action of the electric field, allowing each base of the amplified single strands to gradually pass through the nanopore and generate the electrical signal for each base, and judging the differences in the electrical signals caused by different bases to determine the base sequence of the template nucleic acid.

10. The nanopore sequencing method according to claim 2, wherein the polymerase having a strand displacement activity is selected from phi29 polymerase or Bst polymerase.

11. The nanopore sequencing method according to claim 1, wherein a voltage of the electric field is a millivolt voltage.

12. The nanopore sequencing method according to claim 11, wherein the millivolt voltage is a voltage above 10 mV, preferably a voltage above 50 mV, more preferably a voltage ranging from 100 mV to 250 mV, and most preferably a voltage of 120 mV.

13. The nanopore sequencing method according to claim 1, further comprising a step of preparing the nucleic acid single-stranded loop or the nucleic acid double-stranded loop, wherein the step comprises:
cyclizing a DNA fragment to obtain a single-stranded loop or a double-stranded loop.

14. The nanopore sequencing method according to claim 13, wherein the DNA fragment has a length ranging from 100 bp to 1 Mbp.

15. The nanopore sequencing method according to claim 1, wherein the nanopores are biological nanopores and solid-state nanopores.

16. The nanopore sequencing method according to claim 15, wherein the biological nanopores are protein nanopores, and a narrowest part of the protein nanopores allows a single-stranded nucleic acid to pass through.

17. The nanopore sequencing method according to claim 15, wherein the solid-state nanopores are nanopores of a silicon-based material or a graphene two-dimensional material, and a narrowest part of the nanopores of the silicon-based material allows a single-stranded nucleic acid to pass through.

18. The nanopore sequencing method according to claim 4, wherein the specific modification is selected from a cholesterol modification or a biotin modification;
when the specific modification is the cholesterol modification, the support layer is a phospholipid bilayer, and cholesterol and the phospholipid bilayer are connected through affinity binding; and
when the specific modification is the biotin modification, the support layer comprises a streptavidin modification, and biotin and streptavidin are connected through affinity binding.

19. The nanopore sequencing method according to claim 9, wherein the polymerase is selected from phi29 polymerase or Bst polymerase.

* * * * *

SEQUENCE LISTING

<160> NUMBER OF SEQ ID NOS: 11

<210> SEQ ID NO 1
<211> LENGTH: 67
<212> TYPE: DNA
<213> ORGANISM: Artificial sequence
<220> FEATURE:
<223> OTHER INFORMATION: Synthetic sequence
<220> FEATURE:
<221> NAME/KEY: modified_base
<222> LOCATION: (1)..(1)
<223> OTHER INFORMATION: 5phos

<400> SEQUENCE: 1
agtcggaggc caagcggtct taggaagaca ataggtccga tcaactcctt ggctcacaga        60
acgacat        67

<210> SEQ ID NO 2
<211> LENGTH: 36
<212> TYPE: DNA
<213> ORGANISM: Artificial sequence
<220> FEATURE:
<223> OTHER INFORMATION: Synthetic sequence

<400> SEQUENCE: 2
cttggcucac agaacgacau ggctacgatc cgactt        36

<210> SEQ ID NO 3
<211> LENGTH: 26
<212> TYPE: DNA
<213> ORGANISM: Artificial sequence
<220> FEATURE:
<223> OTHER INFORMATION: Synthetic sequence

<400> SEQUENCE: 3
cttggcucac agaacgacau ggctac        26

<210> SEQ ID NO 4
<211> LENGTH: 26
<212> TYPE: DNA
<213> ORGANISM: Artificial sequence
<220> FEATURE:
<223> OTHER INFORMATION: Synthetic sequence

<400> SEQUENCE: 4
atgtcgttct gugagccaag gagutg        26

<210> SEQ ID NO 5

```
<211> LENGTH: 37
<212> TYPE: DNA
<213> ORGANISM: Artificial sequence
<220> FEATURE:
<223> OTHER INFORMATION: Synthetic sequence
<220> FEATURE:
<221> NAME/KEY: misc_binding
<222> LOCATION: (37)..(37)
<223> OTHER INFORMATION: /iSpC3/-Cholesterol, where /iSpC3/ represents
      -CH2CH2CH2- for block the polymerization of DNA and Cholesterol is
      cholesterol

<400> SEQUENCE: 5
ccgcgtgaga tctgatgatg tttttaaatt tgggttt                              37

<210> SEQ ID NO 6
<211> LENGTH: 82
<212> TYPE: DNA
<213> ORGANISM: Artificial sequence
<220> FEATURE:
<223> OTHER INFORMATION: Synthetic sequence
<220> FEATURE:
<221> NAME/KEY: misc_binding
<222> LOCATION: (1)..(1)
<223> OTHER INFORMATION: /iSpC3/ where /iSpC3/ represents -CH2CH2CH2-.
<220> FEATURE:
<221> NAME/KEY: misc_binding
<222> LOCATION: (13)..(14)
<223> OTHER INFORMATION: /iSpC3/ where /iSpC3/ represents -CH2CH2CH2-.
<220> FEATURE:
<221> NAME/KEY: misc_binding
<222> LOCATION: (65)..(66)
<223> OTHER INFORMATION:
      /iSpC3//iSpC3//iSpC3//iSpC3//iSpC3//iSpC3//iSpC3/ which is for
      purpose of recognition and where each /iSpC3/ represents
      -CH2CH2CH2-
<220> FEATURE:
<221> NAME/KEY: misc_feature
<222> LOCATION: (66)..(82)
<223> OTHER INFORMATION: complementary to the circular DNA

<400> SEQUENCE: 6
aaaaaaacct tccccttccc atcatcatca gatctcacgc ggaaaaaaaa aaaaaaaaa      60 aaaaagaacg acatggctac ga                                             82

<210> SEQ ID NO 7
<211> LENGTH: 17
<212> TYPE: DNA
<213> ORGANISM: Artificial sequence
<220> FEATURE:
<223> OTHER INFORMATION: Synthetic sequence
<220> FEATURE:
<221> NAME/KEY: misc_binding
<222> LOCATION: (17)..(17)
<223> OTHER INFORMATION: cholesterol

<400> SEQUENCE: 7
aaaaaaaaaa aaaaaaa                                                   17

<210> SEQ ID NO 8
<211> LENGTH: 87
<212> TYPE: DNA
<213> ORGANISM: Artificial sequence
<220> FEATURE:
<223> OTHER INFORMATION: Synthetic sequence
<220> FEATURE:
<221> NAME/KEY: modified_base
<222> LOCATION: (1)..(1)
<223> OTHER INFORMATION: 5phos

<400> SEQUENCE: 8
```

```
agtcggaggc caagcggtct taggaagaca ataggtccga tttttttttt tttttttttt          60
tcaactcctt ggctcacaga acgacat                                              87

<210> SEQ ID NO 9
<211> LENGTH: 36
<212> TYPE: DNA
<213> ORGANISM: Artificial sequence
<220> FEATURE:
<223> OTHER INFORMATION: Synthetic sequence

<400> SEQUENCE: 9
cttggcucac agaacgacau ggctacgatc cgactt                                    36

<210> SEQ ID NO 10
<211> LENGTH: 26
<212> TYPE: DNA
<213> ORGANISM: Artificial sequence
<220> FEATURE:
<223> OTHER INFORMATION: Synthetic sequence

<400> SEQUENCE: 10
cttggcucac agaacgacau ggctac                                               26

<210> SEQ ID NO 11
<211> LENGTH: 26
<212> TYPE: DNA
<213> ORGANISM: Artificial sequence
<220> FEATURE:
<223> OTHER INFORMATION: Synthetic sequence

<400> SEQUENCE: 11
atgtcgttct gugagccaag gagutg                                               26
```